United States Patent
Tomokawa et al.

(10) Patent No.: US 8,822,724 B2
(45) Date of Patent: Sep. 2, 2014

(54) METHOD FOR PRODUCING CARBOXYLIC ACID AMIDE

(75) Inventors: Junichi Tomokawa, Itami (JP); Takahiro Kimura, Ibaraki (JP); Norihiko Hirata, Suita (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 65 days.

(21) Appl. No.: 13/812,108

(22) PCT Filed: Jul. 13, 2011

(86) PCT No.: PCT/JP2011/066508
§ 371 (c)(1),
(2), (4) Date: Jan. 24, 2013

(87) PCT Pub. No.: WO2012/014760
PCT Pub. Date: Feb. 2, 2012

(65) Prior Publication Data
US 2013/0123505 A1    May 16, 2013

(30) Foreign Application Priority Data
Jul. 28, 2010 (JP) .................. 2010-168942

(51) Int. Cl.
C07C 231/00 (2006.01)

(52) U.S. Cl.
USPC ........................................ 564/134

(58) Field of Classification Search
USPC ........................................ 564/134
See application file for complete search history.

(56) References Cited

U.S. PATENT DOCUMENTS

2008/0071087 A1  3/2008  Abrecht et al.
2008/0076925 A1  3/2008  Abrecht et al.

FOREIGN PATENT DOCUMENTS

JP    10-059913        3/1998
WO    WO 2004/046143 A1  6/2004
WO    WO 2004/065374 A1  8/2004

OTHER PUBLICATIONS

International Search Report PCT/JP2011/066508 dated Sep. 20, 2011.
Marion G. Gotz et al., "Aza-peptidyl Michael Acceptors. A New Class of Potent and Selective Inhibitors of Asparaginyl Endopeptidases (Legumains) from Evolutionarily Diverse Pathogens", J. Med. Chem. 2008, 51, 2816-2832.
Adrian David et al., "Continuous Process Improvement Toward a Safer Ester Amidation Process", AIChE Spring Nationla Meeting, Conference Proceedings, 98F/1-98F/9, (2005).
Mohamed Ettaoussi et al., "Design and synthesis of benzofuranic derivatives as new ligands at the melatonin-binding site MT3", Bioorganic & Medicinal Chemistry 16, (2008) 4956-4962.
Jagdmann, et al. "A Mild Efficient Procedure for the Conversion of Carboxylic Acid Esters to Primary Amides Using Formamide/Methanolic Sodium Methoxide", Synthetic Communications, 1990, vol. 20, No. 8, pp. 1203-1208.
Office Action in CN Appln No. 201180035857.1 dated Jan. 10, 2014.

*Primary Examiner* — Nizal Chandrakumar
(74) *Attorney, Agent, or Firm* — Foley & Lardner LLP

(57) ABSTRACT

A carboxamide can be produced in a high yield by a method for producing a carboxamide, for example, represented by formula (4):

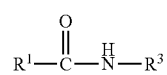

(4)

(wherein $R^1$ and $R^3$ are as defined below), the method comprising a step of allowing a carboxylic acid ester represented by formula (1):

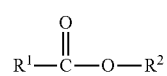

(1)

(wherein $R^1$ represents an optionally substituted $C_1$-$C_{20}$ hydrocarbon group or an optionally substituted $C_3$-$C_{20}$ heterocyclic group, and $R^2$ represents an optionally substituted $C_1$-$C_{20}$ hydrocarbon group), an amine represented by formula (2):

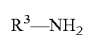

(2)

(wherein $R^3$ represents a hydrogen atom or an optionally substituted $C_1$-$C_{20}$ hydrocarbon group), and a formamide compound represented by formula (3):

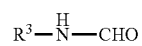

(3)

(wherein $R^3$ is as defined above) to react in the presence of a metal alkoxide.

9 Claims, No Drawings

METHOD FOR PRODUCING CARBOXYLIC ACID AMIDE

TECHNICAL FIELD

The present invention relates to a method for producing a carboxamide.

BACKGROUND ART

Carboxamides are important compounds as a variety of chemical products such as active ingredients of medicines and pesticides, and electronic materials, and synthetic intermediates thereof (see, for example, WO2004/065374).

In WO2004/065374 is disclosed a method in which ethyl 4,5-bis(4-methoxyphenyl)-1,3-oxazole-2-carboxylate, which is a carboxylic acid ester, is allowed to react with formamide in the presence of sodium methoxide, which is a metal alkoxide, to give 4,5-bis(4-methoxyphenyl)-1,3-oxazole-2-carboxamide, which is a carboxamide, in a yield of 71.9% (see Example 2).

However, the method is not necessarily satisfactory in the yield of the carboxamide to be obtained.

Thus, new methods by which a carboxamide can be produced from a carboxylic acid ester in a high yield have been awaited.

SUMMARY OF THE INVENTION

The present invention provides a method for producing a carboxamide, the method comprising allowing a carboxylic acid ester, an amine, and a formamide compound corresponding to the amine to react in the presence of a metal alkoxide. Here, the formamide compound corresponding to the amine means a compound resulting from substitution of one hydrogen atom of the amine by a formyl group.

Particularly, the present invention provides a method for producing a carboxamide represented by formula (4):

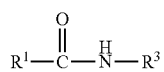
(4)

(wherein $R^1$ and $R^3$ are as defined below), the method comprising a step of allowing a carboxylic acid ester represented by formula (1):

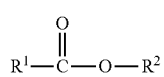
(1)

(wherein $R^1$ represents an optionally substituented $C_1$-$C_{20}$ hydrocarbon group or an optionally substituented $C_3$-$C_{20}$ heterocyclic group, and $R^2$ represent an optionally substituented $C_1$-$C_{20}$ hydrocarbon group),
an amine represented by formula (2):

 (2)

(wherein $R^3$ represent a hydrogen atom or an optionally substituented $C_1$-$C_{20}$ hydrocarbon group), and a formamide compound represented by formula (3):

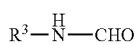
(3)

(wherein $R^3$ is as defined above) to react in the presence of a metal alkoxide.

MODE FOR CARRYING OUT THE INVENTION

Embodiments of the present invention are described in detail below.

Examples of the $C_1$-$C_{20}$ hydrocarbon group represented by $R^1$ in formula (1) include $C_1$-$C_{20}$ aliphatic hydrocarbon groups and $C_6$-$C_{20}$ aromatic hydrocarbon groups.

Examples of the $C_1$-$C_{20}$ aliphatic hydrocarbon groups include $C_1$-$C_{20}$ alkyl groups, $C_2$-$C_{20}$ alkenyl groups, $C_3$-$C_{20}$ cycloalkyl groups, $C_5$-$C_{20}$ cycloalkenyl groups, $C_3$-$C_8$ cycloalkyl groups having up to two $C_1$-$C_6$ alkyl groups, $C_5$-$C_8$ cycloalkenyl groups having up to two $C_1$-$C_6$ alkyl groups, $C_1$-$C_{12}$ alkyl groups having a $C_3$-$C_8$ cycloalkyl group.

Examples of the $C_1$-$C_{20}$ alkyl groups include a methyl group, an ethyl group, a propyl group, an isopropyl group, a butyl group, an isobutyl group, a sec-butyl group, a tert-butyl group, a pentyl group, an isopentyl group, a neopentyl group, a 1-ethylpropyl group, a hexyl group, an isohexyl group, an 1,1-dimethylbutyl group, a 2,2-dimethlylbutyl group, a 3,3-dimethylbutyl group, a 2-ethylbutyl group, a heptyl group, an octyl group, an isooctyl group, a nonyl group, a decyl group, an undecyl group, a dodecyl group, a tridecyl group, and an eicosyl group.

Examples of the $C_2$-$C_{20}$ alkenyl groups include an ethenyl group, a 1-propenyl group, a 2-propenyl group, a 2-methyl-1-propenyl group, a 1-butenyl group, a 2-butenyl group, a 3-butenyl group, a 3-methyl-2-butenyl group, a 1-pentenyl group, a 2-pentenyl group, a 3-pentenyl group, a 4-pentenyl group, a 4-methyl-3-pentenyl group, a 1-hexenyl group, a 3-hexenyl group, a 5-hexenyl group, a 1-heptenyl group, a 1-octenyl group, a 1-nonenyl group, a 1-decenyl group, a 1-undecenyl group, a 1-dodecenyl group, a 1-tridecenyl group, and a 1-eicosenyl.

Examples of the $C_3$-$C_{20}$ cycloalkyl groups include a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group, a cyclotridecyl group, and a cycloeicosyl group.

Examples of the $C_5$-$C_{20}$ cycloalkenyl groups include a 2-cyclopenten-1-yl group, a 3-cyclopenten-1-yl group, a 2-cyclohexen-1-yl group, a 3-cyclohexen-1-yl group, a 2-cyclohepten-1-yl groups, a 2-cycloocten-1-yl group, a 2-cyclononen-1-yl groups, a 2-cyclodecen-1-yl group, a 2-cyclododecen-1-yl groups, a 2-cycloeicosen-1-yl groups, a 2,4-cyclopentadien-1-yl groups, a 2,4-cyclohexadien-1-yl groups, and a 2,5-cyclohexadien-1-yl group.

Examples of the $C_3$-$C_8$ cycloalkyl groups having up to two $C_1$-$C_6$ alkyl groups include a 1-methylcyclopropan-1-yl group, a 2-methylcyclopropan-1-yl group, a 1,2-dimethylcyclopropan-1-yl group, a 2,2-dimethylcyclopropan-1-yl group, a 1-ethylcyclopropan-1-yl group, a 2-ethylcyclopropan-1-yl group, a 1-ethyl-2-methylcyclopropan-1-yl group, a 2-ethyl-2-methylcyclopropan-1-yl group, a 2,2-diethylcyclopropan-yl group, a 2-methylcyclobutan-1-yl group, a 2-methylcyclopentan-1-yl group, a 2-methylcyclohexan-1-yl group, a 2-methylcycloheptan-1-yl group, and a 2-methylcyclooctan-1-yl group.

Examples of the $C_5$-$C_8$ cycloalkenyl groups having up to two $C_1$-$C_6$ alkyl groups include a 1-methyl-2-cyclopenten-1-yl group, a 2-methyl-1-cyclopenten-1-yl group, a 1-methyl-2-cyclohexen-1-yl group, a 2-methyl-1-cyclohexen-1-yl group, a 1-methyl-2-cyclohepten-1-yl group, a 2-methyl-1-cyclohepten-1-yl group, a 1-methyl-2-cyclooecten-1-yl group, and a 2-methyl-1-cyclooecten-1-yl group.

Examples of the $C_1$-$C_{12}$ alkyl groups having a $C_3$-$C_8$ cycloalkyl group include a cyclopropylmethyl group, a 2-(cyclopropyl)ethyl group, a cyclobutylmethyl group, a 2-(cyclobutyl)ethyl group, a cyclopentylmethyl group, a cyclohexylmethyl group, a cycloheptylmethyl group, and a cyclooctylmethyl group.

The $C_6$-$C_{20}$ aromatic hydrocarbon groups herein means hydrocarbon groups having an aromatic ring and examples thereof include a phenyl group, a 1-naphthyl group, a 2-naphthyl group, a phenanthrenyl group, an anthracenyl group, an acenaphthylenyl group, a naphthacenyl group, a biphenylenyl group, a 2-methylphenyl group, a 3-methylphenyl group, a 4-methylphenyl group, a 3,4-dimethylphenyl group, a benzyl group, a (2-methylphenyl)methyl group, a 2-phenylethyl group, a 2-(2-methylphenyl) ethyl group, a 2-phenylcyclopropyl group, and a 4-phenylcyclohexyl group.

The $C_1$-$C_{20}$ hydrocarbon group represented by $R^1$ in formula (1) is optionally substituted, and examples of the substituent include substituents selected from the following <Group P1>:
<Group P1>
$C_1$-$C_{12}$ alkoxy groups, halogen atoms, a nitro group, and a cyano group Examples of the $C_1$-$C_{12}$ alkoxy groups include straight-chain or branched $C_1$-$C_{12}$ alkoxy groups, such as a methoxy group, an ethoxy group, a propoxy group, an isopropoxy group, a butoxy group, an isobutoxy group, a tert-butoxy group, a pentyloxy group, a hexyloxy group, a heptyloxy group, and an octyloxy group, and cyclic $C_3$-$C_{12}$ alkoxy groups, such as a cyclopropoxy group, a cyclobutoxy group, a cyclopentyloxy group, a cyclohexyloxy group, a cycloheptyloxy group, and a cyclooctyloxy group. Examples of the halogen atoms include a fluorine atom, a chlorine atom, and a bromine atom, and the $C_1$-$C_{20}$ hydrocarbon group represented by $R^1$ may have a trifluoromethyl moiety in which there are three fluorine atoms as substituents on one carbon atom.

Examples of the $C_3$-$C_{20}$ heterocyclic group represented by $R^1$ in formula (1) include $C_3$-$C_{20}$ aliphatic heterocyclic groups and $C_3$-$C_{20}$ aromatic heterocyclic groups.

The $C_3$-$C_{20}$ aliphatic heterocyclic groups mean $C_3$-$C_{20}$ heterocyclic groups not having aromaticity and examples thereof include an azetidinyl group, a pyrrolidinyl group, a piperidyl group, an azepanyl group, a piperazinyl group, a morpholinyl group, a thiomorpholinyl group, an oxazolidinyl group, a thiazolydinyl group, an imidazolidinyl group, a oxazolinyl group, an imidazolinyl group, and a pyrazolidinyl group.

The $C_3$-$C_{20}$ aromatic heterocyclic groups mean $C_3$-$C_{20}$ heterocyclic groups having aromaticity and examples thereof include a 2-furyl group, a 3-furyl group, a 2-thienyl group, a 3-pyridyl group, a 2-pyrimidinyl group, a 3-pyridazinyl group, a 2-pyrazinyl group, a 2-pyrrolyl group, a 2-imidazolyl group, a 2-pyrazolyl group, a 2-thiazolyl group, a 2-oxazolyl group, a quinolin-2-yl group, an isoquinoline-1-yl groups, and a benzofuran-2-yl group.

The $C_3$-$C_{20}$ heterocyclic group represented by $R^1$ in formula (1) is optionally substituted, and examples of the substituent include the same substituents as selected from the above-described <Group P1> and a trifluoromethyl group.

Examples of the $C_1$-$C_{20}$ hydrocarbon group in the optionally substituted $C_1$-$C_{20}$ hydrocarbon group represented by $R^2$ in formula (1) include the same as the above-described $C_1$-$C_{20}$ hydrocarbon groups. Examples of the substituent in the $C_1$-$C_{20}$ hydrocarbon group represented by $R^2$ include the same substituents as selected from the above-described <Group P1>.

$R^2$ is preferably a $C_1$-$C_{12}$ alkyl group, more preferably a $C_1$-$C_4$ alkyl group.

Examples of the carboxylic acid ester represented by formula (1) (hereinafter described as carboxylic acid ester (1)) include methyl acetate, methyl propionate, methyl butyrate, methyl valerate, methyl isovalerate, methyl hexanoate, methyl heptanoate, methyl cyclohexanoate, methyl octanoate, methyl isooctanoate, methyl nonanoate, methyl decanoate, methyl cyclopropanecarboxylate, methyl 2,2-dimethylcyclopropanecarboxylate, methyl 2-phenyl-1-cyclopropanecarboxylate, methyl crotonate, methyl 3,3-dimethylacrylate, methyl 3,3-dimethyl-4-pentenoate, methyl 3-cyclohexene-1-carboxylate, methyl benzoate, methyl p-toluylate, methyl 1-naphthoate, methyl 2-naphthoate, methyl 2-chlorobenzoate, methyl 4-chlorobenzoate, methyl 2-bromobenzoate, methyl 4-bromobenzoate, methyl 3-nitrobenzoate, methyl 4-nitrobenzoate, methyl 6-bromo-2-naphthoate, methyl phenylacetate, methyl 4-tolylacetate, methyl 3-phenylpropionate, methyl 1-naphthaleneacetate, methyl 4-methoxyphenylacetate, methyl 3-methoxyphenylacetate, methyl nicotinate, methyl isonicotinate, methyl 6-methylnicotinate, ethyl (R)-(+)-1-ethyl-2-pyrrolidinecarboxylate, methyl 2-pyrazinecarboxylate, methyl nipecotate, methyl isonipecotate, ethyl acetate, propyl acetate, isopropyl acetate, butyl acetate, sec-butyl acetate, tert-butyl acetate, pentyl acetate, isopentyl acetate, hexyl acetate, isohexyl acetate, cyclohexyl acetate, isopropenyl acetate, 2-methylbenzyl acetate, 4-methylbenzyl acetate, 2-chlorobenzyl acetate, 4-chlorobenzyl acetate, 4-methoxybenzyl acetate, 4-nitrobenzyl acetate, phenyl acetate, 1-naphthyl acetate, 2-naphthyl acetate, 2-methyl-1-naphthyl acetate, ethyl propionate, propyl propionate, isopropyl propionate, butyl propionate, sec-butyl propionate, tert-butyl propionate, pentyl propionate, isopentyl propionate, hexyl propionate, isohexyl propionate, cyclohexyl propionate, isopropenyl propionate, 2-methylbenzyl propionate, 4-methylbenzyl propionate, 2-chlorobenzyl propionate, 4-chlorobenzyl propionate, 4-methoxybenzyl propionate, 4-nitrobenzyl propionate, phenyl propionate, 1-naphthyl propionate, 2-naphthyl propionate, 2-methyl-1-naphthyl propionate, ethyl cyclopropanecarboxylate, propyl cyclopropanecarboxylate, isopropyl cyclopropanecarboxylate, butyl cyclopropanecarboxylate, sec-butyl cyclopropanecarboxylate, tert-butyl cyclopropanecarboxylate, pentyl cyclopropanecarboxylate, isopentyl cyclopropanecarboxylate, hexyl cyclopropanecarboxylate, isohexyl cyclopropanecarboxylate, cyclohexyl cyclopropanecarboxylate, isopropenyl cyclopropanecarboxylate, 2-methylbenzyl cyclopropanecarboxylate, 4-methylbenzyl cyclopropanecarboxylate, 2-chlorobenzyl cyclopropanecarboxylate, 4-chlorobenzyl cyclopropanecarboxylate, 4-methoxybenzyl cyclopropanecarboxylate, 4-nitrobenzyl cyclopropanecarboxylate, phenyl cyclopropanecarboxylate, 1-naphthyl cyclopropanecarboxylate, 2-naphthyl cyclopropanecarboxylate, 2-methyl-1-naphthyl cyclopropanecarboxylate, ethyl crotonate, propyl crotonate, isopropyl crotonate, butyl crotonate, sec-butyl crotonate, tert-butyl crotonate, pentyl crotonate, isopentyl crotonate, hexyl crotonate, isohexyl crotonate, cyclohexyl crotonate, isopropenyl crotonate, 2-methylbenzyl crotonate, 4-methylbenzyl crotonate, 2-chlorobenzyl crotonate, 4-chlorobenzyl crotonate, 4-methoxybenzyl crotonate, 4-nitrobenzyl crotonate, phenyl crotonate, 1-naphthyl crotonate, 2-naphthylcrotonate, 2-methyl-1-naphthyl crotonate, ethyl benzoate, propyl benzoate, isopropyl benzoate, butyl benzoate, sec-butyl benzoate, tert-butyl benzoate, pentyl benzoate, isopentyl benzoate, hexyl benzoate, isohexyl benzoate, cyclohexyl benzoate, isopropenyl benzoate, 2-methylbenzyl benzoate, 4-methylbenzyl benzoate, 2-chlorobezyl benzoate, 4-chlorobenzyl benzoate, 4-methoxybenzyl benzoate, 4-nitrobenzyl benzoate, phenyl benzoate, 1-naphthyl benzoate, 2-naphthyl benzoate, 2-methyl-1-naphthyl benzoate, ethyl nicotinate, propyl nicotinate, isopropyl nicotinate, butyl nicotinate, sec-butyl nicotinate, tert-butyl nicotinate, pentyl nicotinate, isopentyl nicotinate, hexyl nicotinate, isohexyl nicotinate, cyclohexyl nicotinate, isopropenyl nicotinate, 2-methylbenzyl nicotinate, 4-methylbenzyl nicotinate, 2-chlorobenzyl nicotinate, 4-chlorobenzyl nicotinate, 4-methoxybenzyl nicotinate, 4-nitrobenzyl nicotinate, phenyl nicotinate, 1-naphthyl nicotinate, 2-naphthyl nicotinate, and 2-methyl-1-naphthyl nicotinate.

The carboxylic acid ester (1) can be synthesized by a known method such as a method in which a carboxylic acid is allowed to react with an acid halogenating agent, such as thionyl chloride, and then the obtained carboxylic halide is allowed to react with an alcohol, and a method in which a carboxylic acid and an alcohol are allowed to react together in the presence of a condensing agent, such as dicyclohexylcarbodiimide. Commercially available products can also be used as they are.

Examples of the $C_1$-$C_{20}$ hydrocarbon group represented by $R^3$ in formulae (2) and (3) include the same as the examples of the above-described $C_1$-$C_{20}$ hydrocarbon group. The $C_1$-$C_{20}$ hydrocarbon group represented by $R^3$ is optionally substituted and examples of the substituent include the same substituents as selected from the above-described <Group P1>.

$R^3$ is preferably a hydrogen atom or a $C_1$-$C_{20}$ alkyl group, more preferably a hydrogen atom or a $C_1$-$C_{12}$ alkyl group, even more preferably a hydrogen atom or a $C_1$-$C_4$ alkyl group.

Examples of the amine represented by formula (2) (hereinafter described as amine (2)) include ammonia, methylamine, ethylamine, propylamine, isopropylamine, cyclopropylamine, butylamine, sec-butylamine, tert-butylamine, pentylamine, isopentylamine, hexylamine, isohexylamine, cyclohexylamine, octylamine, isooctylamine, nonylamine, isononylamine, decylamine, isodecylamine, allylamine, 3-amino-1-butene, propenylamine, 2-methyl-1-propenylamine, 2-methylbenzylamine, 4-methylbenzylamine, 2-chlorobenzylamine, 4-chlorobenzylamine, 4-methoxybenzylamine, 4-nitrobenzylamine, phenylamine, 1-naphthylamine, 2-naphthylamine, and 2-methyl-1-naphthylamine.

The amine (2) is preferably ammonia or a $C_1$-$C_{20}$ alkylamine, more preferably ammonia or a $C_1$-$C_{12}$ alkylamine, even more preferably ammonia or a $C_1$-$C_4$ alkylamine.

The amine (2) can be synthesized according to a known method such as a method in which a nitro compound or a cyano compound is reduced and a method in which an N-substituted phthalimide obtained by allowing a halide and potassium phthalimide to react together is hydrolyzed. Commercially available products can also be used as they are.

Examples of the formamide compound represented by formula (3) (hereinafter described as formamide compound (3)) include formamide, N-methylformamide, N-ethylformamide, N-propylformamide, N-isopropylformamide, N-cyclopropylformamide, N-butylformamide, N-sec-butylformamide, N-tert-butylformamide, N-pentylformamide, N-isopentylformamide, N-hexylformamide, N-isohexylformamide, N-cyclohexylformamide, N-octylformamide, N-isooctylformamide, N-nonylformamide, N-isononylformamide, N-decylformamide, N-isodecylformamide, N-allylformamide, N-propenylformamide, N-2-methyl-1-propenylformamide, N-2-methylbenzylformamide, N-4-methylbenzylformamide, N-2-chlorobnzylformamide, N-4-chlorobenzylformamide, N-4-methoxybenzylformamide, N-4-nitrobenzylformamide, N-phenylformamide, N-1-naphthylformamide, N-2-naphthylformamide, and N-2-methyl-1-naphthylformamide.

The formamide compound (3) can be synthesized according to known methods such as a method in which formic acid is allowed to react with the above-described amine (2) (see, for example, Journal of the American Chemical Society, 1960, Vol. 82, pages 441-443). Commercially available products may also be used as they are.

Examples of the metal alkoxide include alkali metal alkoxides and alkaline earth metal alkoxides, and these metal alkoxides are usually $C_1$-$C_4$ alkoxides.

Examples of the alkali metal alkoxides include lithium alkoxides, such as lithium methoxide, lithium ethoxide, lithium propoxide, lithium isopropoxide, lithium butoxide, lithium sec-butoxide, and lithium tert-butoxide; sodium alkoxides, such as sodium methoxide, sodium ethoxide, sodium propoxide, sodium isopropoxide, sodium butoxide, sodium sec-butoxide, and sodium tert-butoxide; and potassium alkoxides, such as potassium methoxide, potassium ethoxide, potassium propoxide, potassium isopropoxide, potassium butoxide, potassium sec-butoxide, and potassium tert-butoxide.

Examples of the alkaline earth metal alkoxides include magnesium alkoxides, such as magnesium methoxide, magnesium ethoxide, magnesium propoxide, magnesium isopropoxide, magnesium butoxide, magnesium sec-butoxide, and magnesium tert-butoxide; and calcium alkoxides, such as calcium methoxide, calcium ethoxide, calcium propoxide, calcium isopropoxide, calcium butoxide, calcium sec-butoxide, and calcium tert-butoxide.

The metal alkoxide is preferably an alkali metal alkoxide, more preferably sodium methoxide or potassium methoxide.

Next, the method of producing the carboxamide represented by formula (4) (hereinafter described as carboxamide (4)) in the present invention is described. The method of producing the carboxamide (4) has a step in which a carboxylic acid ester (1), an amine (2), and a formamide compound (3) are allowed to react together in the presence of a metal alkoxide. The carboxylic acid ester (1) is converted into a carboxamide (4) by this step. Hereinafter, the reaction of the carboxylic acid ester (1), the amine (2), and the formamide compound (3) may be described as the present reaction.

The amount of the amine (2) used in the present reaction is preferably 1 to 30 mol, more preferably 3 to 15 mol per 1 mol of the carboxylic acid ester (1). By adjusting the amount of the amine (2) used to 1 mol or more per 1 mol of the carboxylic acid ester (1), the carboxamide (4) can be obtained in a high yield even if the amounts of the below-described formamide compound (3) and metal alkoxide used are adjusted to 1 mol or less per 1 mol of the carboxylic acid ester (1). In a practical embodiment, the amount of the amine (2) used is 30 mol or less per 1 mol of the carboxylic acid ester (1).

In the case where ammonia, methylamine, ethylamine, or the like is used as the amine (2) in the present reaction, these can be easily removed and recovered from a reaction mixture by volatilizing them after the completion of the reaction. The amine (2) can be easily removed and recovered from a reaction mixture also by washing a reaction mixture obtained after the completion of the reaction with a mineral acid such as hydrochloric acid and sulfuric acid. Thus, even if the amine (2) is used in excessive amount relative to the carboxylic acid ester (1), the amine (2) can be easily removed and recovered from a reaction mixture after the completion of the reaction. The amine (2) recovered can be refined and reused for the present reaction according to need.

The amount of the formamide compound (3) used is, for example, 0.1 to 10 mol, preferably 0.3 to 1 mol, more preferably 0.4 to 0.9 mol per 1 mol of the carboxylic acid ester (1). When the amount of the formamide compound (3) used is less than 0.1 mol, the advance of the present reaction tends to become slower.

The amount of the metal alkoxide used is, for example, 0.01 to 1 mol, preferably 0.2 to 0.4 mol per 1 mol of the carboxylic acid ester (1). When the amount of the metal alkoxide used is less than 0.01 mol, the advance of the present reaction tends to become slower. Practically, the amount of the metal alkoxide used is adjusted to 1 mol or less.

The present reaction is preferably performed in a solvent.

Examples of the solvent include aliphatic hydrocarbon solvents, aromatic hydrocarbon solvents, halogenated hydrocarbon solvents, ether solvents, alcohol solvents, aprotic polar solvents, and mixed solvents thereof.

Examples of the aliphatic hydrocarbon solvents include hexane, isohexane, heptane, isoheptane, octane, isooctane, nonane, isononane, decane, isodecane, undecane, dodecane, cyclopentane, cyclohexane, methylcyclohexane, and tert-butylhexane; examples of the aromatic hydrocarbon solvents include benzene, toluene, ethylbenzene, isopropylbenzene, tert-butylbenzene, xylene, and mesitylene; examples of the halogenated hydrocarbon solvents include monochlorobenzene, monofluorobenzene, 1,2-dichlorobenzene, 1,3-dichlorobenzene, 1,2,3-trichlorobenzene, dichloromethane, chloroform, and 1,2-dichloroethane; examples of the ether solvents include tetrahydrofuran, diethyl ether, dipropyl ether, diisopropyl ether, dibutyl ether, dipentyl ether, dihexyl ether, diheptyl ether, dioctyl ether, tert-butyl methyl ether, cyclopentyl methyl ether, and diphenyl ether; examples of the alcohol solvents include methanol, ethanol, butyl alcohol, isobutyl alcohol, and tert-butyl alcohol; and examples of the aprotic polar solvents include dimethyl sulfoxide, sulfolane, N,N-dimethylformamide, N,N-dimethylacetamide, N,N-dimethylpropionamide, and N-methylpyrrolidone.

Preferable solvents are alcohol solvents, and methanol is more preferred.

Commercially available solvents can be used as they are and solvents purified by distillation or the like also can be used.

The amount of the solvent to be used is preferably 1 to 100 parts by weight, more preferably 2 parts by weight to 10 parts by weight per 1 part by weight of the carboxylic acid ester (1).

The reaction temperature of the present reaction is, for example, within the range of 0 to 150° C., preferably within the range of 40 to 100° C., more preferably within the range of 60 to 90° C.

The reaction time of the present reaction, which depends upon the amount of the amine (2) used and the reaction temperature, is 1 to 10 hours, for example.

Although the present reaction is performed either under ordinary pressure condition or under increased pressure condition, it is preferably performed under increased pressure condition. The pressure in the present reaction, expressed by gauge pressure, is preferably 0 to 3 MPa, more preferably 0.5 to 1 MPa.

The present reaction can be performed by, for example, any one of the methods described in (I) to (VIII) below.

(I) A method in which a metal alkoxide and a formamide compound (3) are added to a carboxylic acid ester (1), then an amine (2) is added to the mixture obtained, and the temperature of the resulting mixture is adjusted to the above-described reaction temperature.

(II) A method in which a metal alkoxide and a formamide compound (3) are added to a carboxylic acid ester (1), then the temperature of the mixture obtained is adjusted to the above-described reaction temperature, and an amine (2) is added thereto.

(III) A method in which an amine (2) and a metal alkoxide are added to a carboxylic acid ester (1), then a formamide compound (3) is added to the mixture obtained, and the temperature of the resulting mixture is adjusted to the above-described reaction temperature.

(IV) A method in which an amine (2) and a metal alkoxide are added to a carboxylic acid ester (1), then the temperature of the mixture obtained is adjusted to the above-described reaction temperature, and a formamide compound (3) is added thereto.

(V) A method in which an amine (2) and a formamide compound (3) are added to a carboxylic acid ester (1), then a metal alkoxide is added to the mixture obtained, and the temperature of the resulting mixture is adjusted to the above-described reaction temperature.

(VI) A method in which an amine (2) and a formamide compound (3) are added to a carboxylic acid ester (1), then the temperature of the mixture obtained is adjusted to the above-described reaction temperature, and a metal alkoxide is added thereto.

(VII) A method in which a metal alkoxide and a formamide compound (3) are added to an amine (2), then a carboxylic acid ester (1) is added to the mixture obtained, and the temperature of the resulting mixture is adjusted to the above-described reaction temperature.

(VIII) A method in which a metal alkoxide and a formamide compound (3) are added to an amine (2), then the temperature of the mixture obtained is adjusted to the above-described reaction temperature, and a carboxylic acid ester (1) is added thereto.

The progress of the present reaction can be checked by analysis means, such as thin layer chromatography, gas chromatography, and high performance liquid chromatography.

After the end of the present reaction, a carboxamide (4) can be isolated by optionally subjecting the resulting reaction mixture to concentration treatment, then applying post treatment, such as filtration, extraction, and rinsing, to the mixture, and then performing isolation treatment, such as distillation and crystallization. The carboxamide (4) isolated can be purified by purification treatment, such as recrystallization; extraction purification; distillation; adsorption treatment to activated carbon, silica, alumina, etc.; and chromatography such as silica gel column chromatography.

Examples of the carboxamide (4) to be obtained include acetamide, propionamide, butyramide, valeramide, isovaleramide, hexanamide, heptanamide, cyclohexylamide, octanamide, isooctanamide, nonanamide, decanamide, cyclopropanecarboxamide, 2,2-dimethylcyclopropanecarboxamide, 2-phenyl-1-cyclopropanecarboxamide, crotonamide, methacrylamide, 3,3-dimethylpentenamide, 3-cyclohexene-1-carboxamide, benzamide, 4-toluamide, 1-naphthamide, 2-naphthamide, 2-chlorobenzamide, 4-chlorobenzamide, 2-bromobenzamide, 4-bromobenzamide, 3-nitrobenzamide, 4-nitrobenzamide, 6-bromo-1-naphthamide, 2-phenylacetamide, 4-tolyl-2-acetamide, 3-phenylpropionamide, 1-naphthalenecarboxamide, 4-methoxyphenylcarboxamide, 3-methoxyphenylcarboxamide, nicotinamide, isonicotinamide, 6-methylnicotinamide, (R)-(+)-1-ethyl-2-pyrrolidinecarboxamide, 2-pyrazinecarboxamide, nipecotamide, isonipecotamide, N-methylacetamide, N-methylvaleramide, N-phenylacetamide, and N-phenylmethylvaleramide.

EXAMPLES

The present invention will be described below in more detail with reference to Examples.

Example 1

Production of 2,2-dimethylcyclopropanecarboxamide

A 200-mL autoclave equipped with a stirring blade was flushed with nitrogen and then was charged with 10.00 g (70.3 mmol) of ethyl 2,2-dimethylcyclopropanecarboxylate, 2.22 g (49.3 mmol) of formamide, 5.42 g (28.1 mmol) of a 28% sodium methoxide solution in methanol, and 25.00 g of methanol at ordinary temperature. Then, the pressure was increased to 0.2 MPa (gauge pressure) by blowing ammonia gas into the autoclave. The resulting mixture was heated to 80° C. and was stirred at this temperature for 5 hours. Then, the reaction mixture was cooled to ordinary temperature to give 49.86 g of a reaction mixture containing 2,2-dimethylcyclopropanecarboxamide. The reaction mixture was analyzed by high performance liquid chromatography (column: CAPCELLPAK C18 MGIII, produced by Shiseido Co., Ltd.) and was quantified using authentic 2,2-dimethylcyclopropanecarboxamide prepared separately. As a result, the resulting reaction mixture was found to contain 7.41 g (65.51 mmol) of 2,2-dimethylcyclopropanecarboxamide. The yield was 93%.

Referential Example 1

Purification of 2,2-dimethylcyclopropanecarboxamide

For use as a synthetic intermediate of medicament, the resulting 2,2-dimethylcyclopropanecarboxamide was purified by the following method.

Methanol was evaporated from the reaction mixture under reduced pressure, and to the residue was added 31.80 g of water. The mixture obtained was extracted twice with methyl isobutyl ketone (hereinafter abbreviated as MIBK) (32.57 g, 9.80 g) at 65° C. The organic layers obtained were combined and the combined organic layer was washed with 5.71 g of water to give 43.27 g of MIBK solution containing 2,2-dimethylcyclopropanecarboxamide. The solution was quantified in the same manner as described above. The resulting MIBK solution was found to contain 6.24 g (55.2 mmol) of 2,2-dimethylcyclopropanecarboxamide. This solution was cooled to 25° C. under stirring and the solid that precipitated out was taken by filtration. The filtrate obtained at this time was concentrated to 15.63 g under reduced pressure. The concentrated mixture was cooled to 15° C. under stirring and then the solid that precipitated out was taken by filtration. By the two crystallization operations, 4.67 g (41.3 mmol, yield after purification =59%) with 100% content was obtained, which is suitable as a synthetic intermediate of a medicament.

Example 2

Production of 2,2-dimethylcyclopropanecarboxamide

A 1000-mL autoclave equipped with a stirring blade was flushed with nitrogen and then was charged with 48.30 g (340 mmol) of ethyl 2,2-dimethylcyclopropanecarboxylate, 11.08 g (246 mmol) of formamide, 27.04 g (140 mmol) of a 28% sodium methoxide solution in methanol, and 125.08 g of methanol at ordinary temperature. Then, the pressure was increased to 0.2 MPa (gauge pressure) by blowing ammonia gas into the autoclave. The resulting mixture was heated to 80° C. and was stirred at this temperature for 5 hours. Then, the reaction mixture was cooled to ordinary temperature to give 252.96 g of a reaction mixture containing 2,2-dimethylcyclopropanecarboxamide. The reaction mixture was analyzed by high performance liquid chromatography (column: CAPCELLPAK C18 MGIII, produced by Shiseido Co., Ltd.) and was quantified using authentic 2,2-dimethylcyclopropanecarboxamide prepared separately. As a result, the resulting reaction mixture was found to contain 35.50 g (314 mmol) of 2,2-dimethylcyclopropanecarboxamide. The yield was 92%.

Example 3

Production of Crotonamide

In accordance with the method described in Example 2 except for using a 200-mL autoclave instead of the 1000-mL autoclave in Example 2, 5.00 g (49.9 mmol) of methyl crotonate instead of ethyl 2,2-dimethylcyclopropanecarboxylate and using 1.57 g (34.9 mmol) of formamide, 3.85 g (20.0 mmol) of a 28% sodium methoxide solution in methanol, and 12.50 g of methanol, 25.35 g of a reaction mixture containing crotonamide. The reaction mixture was analyzed by gas chromatography (column: DB-WAX, produced by Agilent Technologies, Inc.) and was quantified using authentic crotonamide prepared separately. As a result, the resulting reaction mixture was found to contain 0.99 g (11.6 mmol) of crotonamide and 2.44 g (28.7 mmol) of cis-2-butenamide, which is an isomer of crotonamide. The yield of crotonamide was 23% and the yield of cis-2-butenamide, which is an isomer of crotonamide, was 57%. The combined yield of these isomers was 80%.

Example 4

Production of Valeramide

In accordance with the method described in Example 3 except for using 5.00 g (43.0 mmol) of methyl valerate instead of methyl crotonate in Example 3 and using 1.36 g (30.2 mmol) of formamide and 3.32 g (17.2 mmol) of a 28% sodium methoxide solution in methanol, 25.07 g of a reaction mixture containing valeramide. The reaction mixture was analyzed by gas chromatography (column: DB-WAX, produced by Agilent Technologies, Inc.) and was quantified using authentic valeramide prepared separately. As a result, the resulting reaction mixture was found to contain 4.34 g (42.9 mmol) of valeramide. The yield was 100%.

Example 5

Production of Benzamide

In accordance with the method described in Example 3 except for using 5.00 g (36.72 mmol) of methyl benzoate instead of methyl crotonate in Example 3 and using 1.16 g (25.75 mmol) of formamide and 2.83 g (14.67 mmol) of a 28% sodium methoxide solution in methanol, 24.53 g of a reaction mixture containing benzamide. The reaction mixture was analyzed by high performance liquid chromatography (column: CAPCELLPAK C18 MGIII, produced by Shiseido Co., Ltd.) and was quantified using standard benzamide prepared separately. As a result, the resulting reaction mixture was found to contain 4.23 g (41.8 mmol) of benzamide. The yield was 97%.

Example 6

Production of Nicotinamide

In accordance with the method described in Example 3 except for using 5.00 g (36.46 mmol) of methyl nicotinate instead of methyl crotonate in Example 3 and using 1.15 g (25.52 mmol) of formamide and 2.81 g (14.58 mmol) of a 28% sodium methoxide solution in methanol, 25.22 g of a reaction mixture containing nicotinamide. The reaction mixture was analyzed by high performance liquid chromatography (column: CAPCELLPAK C18 MGIII, produced by Shiseido Co., Ltd.) and was quantified using authentic nicotinamide prepared separately. As a result, the resulting reaction mixture was found to contain 3.82 g (31.3 mmol) of nicotinamide. The yield was 86%.

Example 7

Production of trans-2-phenyl-1-cyclopropanecarboxamide

In accordance with the method described in Example 3 except for using 1.44 g (8.17mmol) of methyl trans-2-phenyl-1-cyclopropanecarboxylate instead of methyl crotonate in Example 3 and using 1.15 g (5.72 mmol) of formamide and 2.81 g (3.27 mmol) of a 28% sodium methoxide solution in methanol, 21.84 g of a reaction mixture containing trans-2-phenyl-1-cyclopropanecarboxamide. The reaction mixture was analyzed by high performance liquid chromatography and was quantified using authentic trans-2-phenyl-1-cyclopropanecarboxamide prepared separately. As a result, the resulting reaction mixture was found to contain 1.18 g (7.32 mmol) of trans-2-phenyl-1-cyclopropanecarboxamide. The yield was 90%.

Example 8

Production of N-methylvaleramide

A 200-mL autoclave equipped with a stirring blade was flushed with nitrogen and then was charged with 5.00 g (43.0 mmol) of methyl valerate, 1.78 g (30.1 mmol) of N-methylformamide, 3.32 g (17.2 mmol) of a 28% sodium methoxide solution in methanol, and 12.50 g (161 mmol) of a 40% methylamine solution in methanol. The resulting mixture was heated to 80° C. and stirred at this temperature for 5 hours to give 22.87 g of a reaction mixture containing N-methylvaleramide. The reaction mixture was analyzed by gas chromatography and was quantified using authentic N-methylvaleramide prepared separately. As a result, the resulting reaction mixture was found to contain 4.75 g (41.2 mmol) of N-methylvaleramide. The yield was 96%.

Industrial Applicability

Carboxamides are compounds important as a variety of chemical products such as active ingredients of medicines and pesticides, and electronic materials, and synthetic intermediates thereof. The present invention can be used as a method for producing a carboxamide.

The invention claimed is:

1. A method for producing a carboxamide, the method comprising allowing a carboxylic acid ester, an amine, and a formamide compound corresponding to the amine to react in the presence of a metal alkoxide, wherein the carboxamide is represented by formula (4):

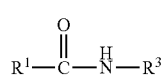

(4)

wherein $R^1$ and $R^3$ are as defined below,
the method comprising a step of allowing a carboxylic acid ester represented by formula (1):

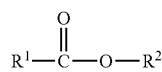

(1)

wherein $R^1$ represents an optionally substituted $C_1$-$C_{20}$ hydrocarbon group or an optionally substituted $C_3$-$C_{20}$ heterocyclic group, and $R^2$ represents an optionally substituted $C_1$-$C_{20}$ hydrocarbon group,
an amine represented by formula (2):

(2)

wherein $R^3$ represents a hydrogen atom or an optionally substituted $C_1$-$C_{20}$ hydrocarbon group,
and a formamide compound represented by formula (3):

(3)

wherein $R^3$ is as defined above.

2. The method according to claim 1, wherein the step is a step of performing the reaction in a solvent.

3. The method according to claim 2, wherein the solvent is an alcohol solvent.

4. The method according to claim 1, wherein the metal alkoxide is an alkali metal alkoxide.

5. The method according to claim 1, wherein the step is a step performed under an increased pressure condition.

6. The method according to claim 1, wherein $R^3$ in each of formulae (2), (3) and (4) is a hydrogen atom or a $C_1$-$C_{12}$ alkyl group.

7. The method according to claim 1, wherein $R^2$ in formula (1) is a $C_1$-$C_{12}$ alkyl group.

8. The method according to claim 2, wherein the metal alkoxide is an alkali metal alkoxide.

9. The method according to claim 2, wherein the step is a step performed under an increased pressure condition.

* * * * *